(12) United States Patent
Takatsu et al.

(10) Patent No.: US 7,531,361 B2
(45) Date of Patent: May 12, 2009

(54) COLORATION AGENT FOR CARBONYL SULFIDE, DETECTING MEANS AND FUEL CELL SYSTEM

(75) Inventors: Kozo Takatsu, Chiba (JP); Gakuji Takegoshi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 249 days.

(21) Appl. No.: 11/659,965

(22) PCT Filed: Aug. 5, 2005

(86) PCT No.: PCT/JP2005/014423

§ 371 (c)(1),
(2), (4) Date: Feb. 12, 2007

(87) PCT Pub. No.: WO2006/016533

PCT Pub. Date: Feb. 16, 2006

(65) Prior Publication Data

US 2008/0081374 A1    Apr. 3, 2008

(30) Foreign Application Priority Data

Aug. 11, 2004    (JP) ............................. 2004-234628

(51) Int. Cl.
*G01N 31/22*    (2006.01)
(52) U.S. Cl. ...................... 436/126; 436/119; 436/120; 436/128
(58) Field of Classification Search ................ 436/126, 436/119, 120, 128; 423/244, 247, 437, 573
See application file for complete search history.

(56) References Cited

U.S. PATENT DOCUMENTS 3,412,038 A * 11/1968 Plantz ........................ 436/120

(Continued)

FOREIGN PATENT DOCUMENTS

EP    0 804 959 A1    11/1997

(Continued)

OTHER PUBLICATIONS

U.S. Appl. No. 11/659,964, filed Feb. 12, 2007, Takatsu, et al.

(Continued)

*Primary Examiner*—Jill Warden
*Assistant Examiner*—Rebecca Fritchman
(74) *Attorney, Agent, or Firm*—Oblon, Spivak, McClelland, Maier & Neustadt, P.C.

(57) ABSTRACT

Provided are a coloration agent for carbonyl sulfide which contains a metal oxide, and at least one metal component selected from among a cerium component, a silver component, a copper component, a nickel component, and an iron component, the metal component being supported on the metal oxide, or which contains at least one metal oxide selected from among a cerium oxide, a silver oxide, a copper oxide, a nickel oxide, and an iron oxide; carbonyl sulfide detection means including the coloration agent for carbonyl sulfide; and a fuel cell system including the detection means. The coloration agent for carbonyl sulfide has the ability to develop a color in the presence of carbonyl sulfide even at ambient temperature, exhibits excellent performance in detecting carbonyl sulfide contained in a hydrocarbon fuel, and enables the service life of a desulfurizing agent to be determined through visual observation.

3 Claims, 1 Drawing Sheet

U.S. PATENT DOCUMENTS

| | | | | |
|---|---|---|---|---|
| 4,977,093 | A | * | 12/1990 | Cooke .................. 436/119 |
| 5,080,867 | A | * | 1/1992 | Cooke .................. 422/86 |
| 5,177,050 | A | * | 1/1993 | Schubert .................. 502/415 |
| 5,219,542 | A | * | 6/1993 | Lowery et al. .............. 423/230 |
| 5,360,468 | A | * | 11/1994 | Schubert .................. 95/136 |

FOREIGN PATENT DOCUMENTS

| | | |
|---|---|---|
| JP | 05 164753 | 6/1993 |
| JP | 6 7127 | 1/1994 |
| JP | 10 115582 | 5/1998 |
| JP | 2001 305123 | 10/2001 |
| JP | 2003 035705 | 2/2003 |
| JP | 2004 163371 | 6/2004 |
| JP | 2005 043186 | 2/2005 |

OTHER PUBLICATIONS

U.S. Appl. No. 08/809,293, filed Mar. 27, 1997, Takatsu, et al.

Michael Anderson, et al., "Field Analysis of Trace Sulfur Compounds in Hydrocarbon Gas Streams", Proceedings of the Seventy-Fourth GPA Annual Convention, pp. 328-336, 1995.

Fumihiko Kiso, et al., "Eagle Project for IGFC in Japan", 25th International Conference on Coal Utilization & Fuel Systems, pp. 297-305, 2000.

* cited by examiner

[Fig 1]
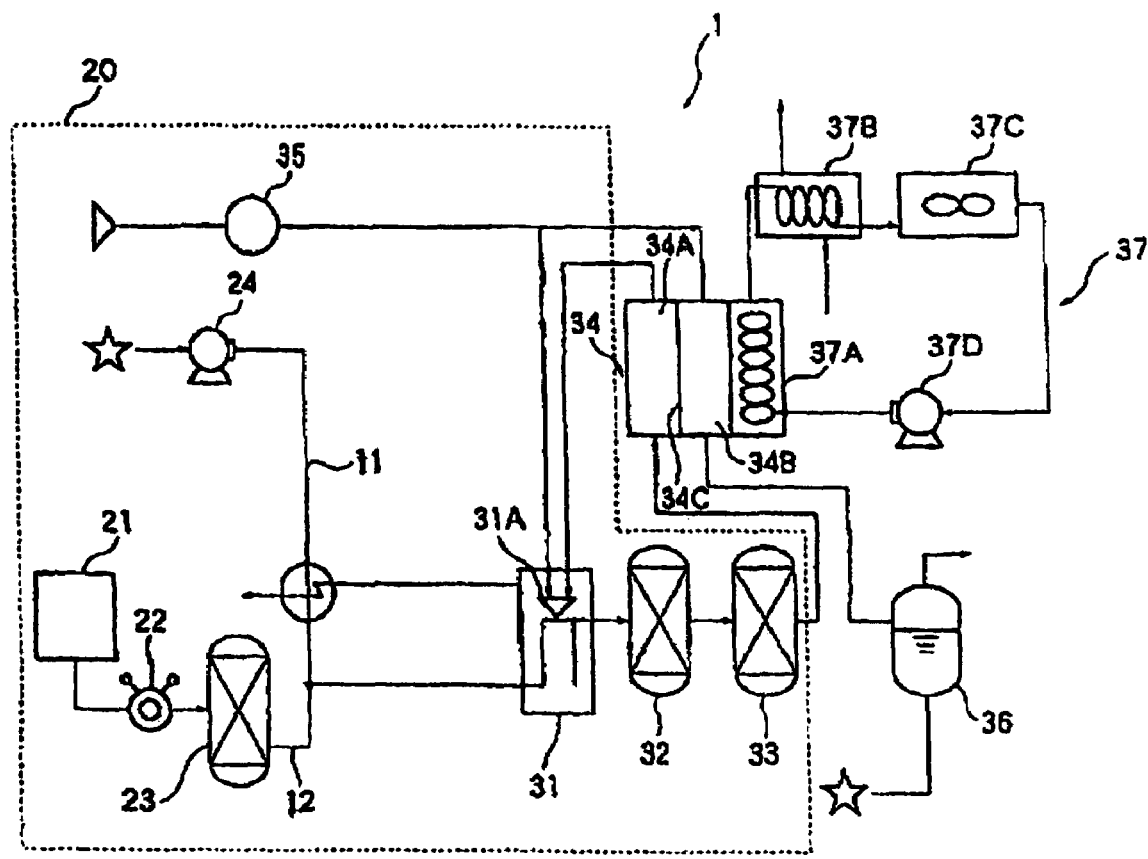

COLORATION AGENT FOR CARBONYL SULFIDE, DETECTING MEANS AND FUEL CELL SYSTEM

TECHNICAL FIELD

The present invention relates to a coloration agent for carbonyl sulfide; to carbonyl sulfide detection means including the coloration agent for carbonyl sulfide; and to a fuel cell system including the detection means. More particularly, the present invention relates to a coloration agent for carbonyl sulfide containing a metal oxide and, supported on the metal oxide, at least one metal component selected from among a cerium component, a silver component, a copper component, a nickel component and an iron component; to a coloration agent for carbonyl sulfide containing at least one oxide selected from among a cerium oxide, a silver oxide, a copper oxide, a nickel oxide, and an iron oxide; to carbonyl sulfide detection means including such a coloration agent for carbonyl sulfide; and to a fuel cell system including the detection means.

BACKGROUND ART

In the case where hydrogen for fuel cells is produced through reforming of a hydrocarbon fuel (e.g., kerosene, LPG, or city gas), in order to reduce poisoning of a reforming catalyst, the sulfur content of the hydrocarbon fuel must be maintained at a low level of 0.05 ppm or less over a long period of time.

Similar to the above-described case, when propylene or butene is employed as a raw material of a petrochemical product, in order to prevent poisoning of a catalyst, the sulfur content of the propylene or butene must be reduced to 0.05 ppm or less.

LPG contains, in addition to sulfur compounds such as methanethiol and carbonyl sulfide (COS), another class of sulfur compounds that have been added as odorants, such as dimethyl sulfide (DMS), 2-methyl-2-propanethiol, and methyl ethyl sulfide (MES). A variety of adsorbents have been proposed for removing sulfur, through adsorption, from such a fuel gas (e.g., LPG or city gas), and prediction of the service life of such an adsorbent is important for the aforementioned purpose.

As has been known, a sulfur compound is detected on the basis of change in color of a zeolite adsorbent (see, for example, Patent Document 1). However, carbonyl sulfide has conventionally been difficult to detect by color testing.

Patent Document 1: Japanese Patent Application Laid-Open (kokai) No. 2001-305123

DISCLOSURE OF THE INVENTION

In view of the foregoing, an object of the present invention is to provide a coloration agent for carbonyl sulfide which facilitates visual detection of carbonyl sulfide contained in a hydrocarbon compound or an oxygen-containing hydrocarbon compound. Another object of the present invention is to provide carbonyl sulfide detection means comprising the coloration agent for carbonyl sulfide. Yet another object of the present invention is to provide a fuel cell system comprising the detection means.

In order to solve the aforementioned problems, the present inventors have conducted extensive studies, and as a result have found that a coloration agent for carbonyl sulfide containing a metal oxide and, at least one metal component selected from among a cerium component, a silver component, a copper component, a nickel component, and an iron component, the metal component being supported on the metal oxide, or a coloration agent for carbonyl sulfide containing at least one oxide selected from among a cerium oxide, a silver oxide, a copper oxide, a nickel oxide, and an iron oxide has the ability to develop a color in the presence of carbonyl sulfide even at ambient temperature. The present inventors have also found that such a coloration agent exhibits excellent performance in detecting carbonyl sulfide contained in a hydrocarbon compound, and enables the service life of a desulfurizing agent to be determined through visual observation. The present invention has been accomplished on the basis these findings.

Accordingly, the present invention provides:

(1) A coloration agent for carbonyl sulfide comprising a metal oxide and, supported on the metal oxide, at least one metal component selected from among a cerium component, a silver component, a copper component, a nickel component, and an iron component;

(2) The coloration agent for carbonyl sulfide as described in (1) above, wherein the metal oxide is at least one metal oxide or metal composite oxide selected from among ceria, alumina, silica, silica-alumina, zirconia, titania, and magnesia;

(3) A coloration agent for carbonyl sulfide comprising at least one oxide selected from among a cerium oxide, a silver oxide, a copper oxide, a nickel oxide, and an iron oxide;

(4) Carbonyl sulfide detection means for use in desulfurization of a carbonyl-sulfide-containing hydrocarbon compound, characterized in that the means comprises a coloration agent for carbonyl sulfide as recited in any of (1) to (3) above; and (5) A fuel cell system comprising carbonyl sulfide detection means as recited in (4) above.

According to the present invention, there can be provided a coloration agent for carbonyl sulfide which has the ability to develop a color in the presence of carbonyl sulfide even at ambient temperature, which exhibits excellent performance in detecting carbonyl sulfide contained in a hydrocarbon compound or an oxygen-containing hydrocarbon compound, and which enables the service life of a desulfurizing agent to be determined through visual observation; carbonyl sulfide detection means comprising the coloration agent for carbonyl sulfide; and a fuel cell system comprising the detection means.

BRIEF DESCRIPTION OF THE DRAWING

FIG. 1 is a schematic representation showing an embodiment of the fuel cell system of the present invention including the carbonyl sulfide detection means of the present invention.

DESCRIPTION OF REFERENCE NUMERALS

1: Fuel cell system
11: Water supply pipe
12: Fuel feed pipe
20: Hydrogen production system
21: Fuel tank
22: Regulator
23: Desulfurizer with carbonyl sulfide detection means
24: Water pump
31: Reformer
31A: Burner
32: Carbon monoxide shift reactor
33: Carbon monoxide preferential oxidation reactor
34: Fuel cell 34A: Anode
34B: Cathode
34C: Polymer electrolyte
35: Air blower
36: Gas-water separator
37: Exhaust heat recovery apparatus
37A: Heat exchanger
37B: Heat exchanger
37C: Condenser
37D: (Circulation) pump

BEST MODES FOR CARRYING OUT THE
INVENTION

The coloration agent for carbonyl sulfide of the present invention—which contains a carrier (e.g., silica, alumina, titania, or zirconia), and at least one metal component selected from among a cerium component, a copper component, a nickel component, and an iron component, the metal component being supported on the carrier, or which contains at least one oxide selected from among a cerium oxide, a copper oxide, a nickel oxide, and an iron oxide (e.g., an oxide such as cerium oxide)—preferably has a specific surface area of 50 m$^2$/g or more. The specific surface area is particularly preferably 70 m$^2$/g or more, more preferably 90 m$^2$/g or more, much more preferably 100 m$^2$/g or more. When the specific surface area is small, leakage of a carbonyl-sulfide-containing gas toward the downstream side could occur before color development. The amount (as reduced to elemental metal) of the metal component or oxide contained in the coloration agent for carbonyl sulfide is generally 3 mass % or more, preferably 10 mass % or more. When the amount as reduced to elemental metal is small, leakage of a carbonyl-sulfide-containing gas toward the downstream side could occur before color development. No particular limitation is imposed on the maximum of the amount as reduced to elemental metal, but the maximum is generally about 80 mass %. The metal component contained in the coloration agent for carbonyl sulfide is preferably a cerium component.

Similarly, the coloration agent for carbonyl sulfide which contains a carrier and a silver component supported on the carrier or which contains a silver oxide, preferably has a specific surface area of 50 m$^2$/g or more. The specific surface area is particularly preferably 70 m$^2$/g or more, more preferably 90 m$^2$/g or more, much more preferably 100 m$^2$/g or more. When the specific surface area is small, leakage of a carbonyl-sulfide-containing gas toward the downstream side could occur before color development. A particularly preferred coloration agent for carbonyl sulfide contains a carrier (e.g., alumina, silica, titania, or zirconia) and a silver component supported on the carrier. The carrier employed is particularly preferably alumina. The amount (as reduced to elemental metal) of the silver component contained in the coloration agent for carbonyl sulfide is preferably 1 to 30 mass %, more preferably 3 to 10 mass %, much more preferably 5 to 10 mass %. When the amount of the silver component is small, leakage of a carbonyl-sulfide-containing gas toward the downstream side could occur before development of color. In contrast, when the amount of the silver component is excessively large, aggregation of silver occurs, and the color of the resultant coloration agent for carbonyl sulfide is changed into black, which may cause difficulty in determining the degree of color development.

No particular limitation is imposed on the method for supporting, on a metal oxide, at least one metal component selected from among a cerium component, a silver component, a copper component, a nickel component, and an iron component. Examples of the supporting method include a method in which at least one metal oxide or metal composite oxide selected from among alumina, silica, silica-alumina, zirconia, titania, and magnesia is impregnated with an aqueous solution prepared by dissolving a predetermined amount of a salt of the aforementioned metal component in water so that the metal component is supported on the metal oxide or metal composite oxide, followed by drying at about 50 to about 120° C. and subsequent heating to about 300 to about 600° C. for calcination.

The aforementioned at least one oxide selected from among a cerium oxide, a silver oxide, a copper oxide, a nickel oxide, and an iron oxide is prepared through, for example, the following procedure: an aqueous alkali solution (e.g., an aqueous sodium hydroxide solution) is added dropwise to an aqueous solution prepared by dissolving a predetermined amount of the aforementioned metal salt in water so that the pH of the resultant mixture is maintained at 10 or more; the mixture is stirred for about one to about five hours while the temperature of the mixture is maintained at 50 to 60° C., to thereby precipitate a solid product; the solid product is separated through filtration and then washed with water; and the solid product is dried at about 100 to about 150° C. for about 10 to about 20 hours, followed by calcination at about 300 to about 600° C. and pulverization of the thus-calcined product. The resultant powder may be melt-kneaded with fibrous polymer, cellulose, or the like, and then extruded through extrusion molding or a similar technique, followed by crushing, to thereby yield a coloration agent for carbonyl sulfide of predetermined size.

The carbonyl sulfide detection means of the present invention may be any of the following systems: (I) a system in which carbonyl sulfide is detected by use of a mixture of the coloration agent for carbonyl sulfide of the present invention and a desulfurizing agent; (II) a detection system in which detection means filled with the coloration agent for carbonyl sulfide is provided downstream of a desulfurizer filled with a desulfurizing agent; i.e., a system in which the desulfurizing agent and the coloration agent for carbonyl sulfide are provided so that a carbonyl-sulfide-containing hydrocarbon compound flows from the desulfurizing-agent-filled desulfurizer to the coloration agent for carbonyl sulfide-filled detection means; and (III) a system in which the coloration agent for carbonyl sulfide is sandwiched between two desulfurizing agents in a single container so that a carbonyl-sulfide-containing hydrocarbon compound flows from one of the desulfurizing agents through the coloration agent for carbonyl sulfide to the other desulfurizing agent.

In the case where the detection means is in the form of a system in which carbonyl sulfide is detected by use of a mixture of the coloration agent for carbonyl sulfide and a desulfurizing agent, the entirety of a desulfurizer may be formed of a transparent tube, or the main body of the desulfurizer may be formed of a non-transparent tube which has a transparent portion. In the case where a desulfurizer and coloration agent for carbonyl sulfide-filled detection means are separately provided, the desulfurizer may be formed of a non-transparent tube and the detection means may be formed of a transparent tube. The aforementioned transparent tube can be formed from a plastic material (e.g., acrylic resin) or a transparent material (e.g., glass), whereas the non-transparent tube can be formed from, for example, a stainless steel material. The non-transparent tube may have a belt-like transparent portion provided in a direction of flow of a hydrocarbon compound, or may have a transparent portion provided on a circumferential portion in a direction perpendicular to the flow direction. The material of the transparent portion may be, for example, a transparent plastic material (e.g., acrylic resin) or glass. When the aforementioned transparent portion is provided on a desulfurizer formed of a non-transparent tube, preferably, the transparent portion is provided at least in the vicinity of the outlet of the desulfurizer. This is because, since adsorption of carbonyl sulfide onto a desulfurizing agent proceeds from the raw fuel inlet of the desulfurizer toward the outlet thereof, whether or not the desulfurizing agent is usable can be readily determined through detection of change in color attributed to adsorption of carbonyl sulfide onto the desulfurizing agent provided in the vicinity of the desulfurizer outlet. Also, in the case where a hydrocarbon fuel containing a sulfur compound other than carbonyl sulfide (e.g., methanethiol, dimethyl sulfide (IDMS), or methyl ethyl sulfide) is subjected to desulfurization, whether or not the desulfurizing agent is usable can be determined through detection of change in color attributed to adsorption of the sulfur-compound-containing hydrocarbon fuel onto the desulfurizing agent.

A carbonyl-sulfide-containing gas such as a hydrocarbon compound or LPG is caused to flow through the desulfurizer under the following operation conditions: temperature: −50 to 350° C., gas hourly space velocity (GHSV): 100 to 300,000 $h^{-1}$ FIG. 1 is a schematic representation showing an embodiment of the fuel cell system of the present invention including the carbonyl sulfide detection means of the present invention. The fuel cell system of the present invention will next be described with reference to FIG. 1 (accompanying drawing).

In this embodiment, the fuel cell system of the present invention is applied to a polymer electrolyte fuel cell. However, the fuel cell system can also be applied to another type of fuel cell (e.g., a solid oxide fuel cell).

As shown in FIG. 1, a hydrocarbon compound contained in a fuel tank 21 is, if necessary, depressurized by means of a regulator 22, and then is fed into a desulfurizer 23. The interior of the desulfurizer can be filled with a desulfurizing agent and the coloration agent of the present invention. The hydrocarbon compound which has undergone desulfurization in the desulfurizer 23 is mixed with water which has been fed from a water tank through a water pump 24. The resultant mixture is fed into a reformer 31 after vaporization of water.

The interior of the reformer 31 is filled with a hydrocarbon reforming catalyst. The hydrocarbon-compound-containing mixture (i.e., mixture of water vapor, oxygen, and the hydrocarbon compound) is introduced into the reformer 31, and subjected to reforming reaction, to thereby produce hydrogen gas.

The thus-produced hydrogen gas is caused to pass through a carbon monoxide shift reactor 32 and a carbon monoxide preferential oxidation reactor 33, and the CO content of the hydrogen gas is reduced to such a level that does not affect properties of a fuel cell. Examples of the catalyst which may be employed in the carbon monoxide shift reactor 32 include an iron-chromium catalyst, a copper-zinc catalyst, and a noble metal catalyst. Examples of the catalyst which may be employed in the carbon monoxide preferential oxidation reactor 33 include a ruthenium catalyst, a platinum catalyst, and a mixture thereof.

A polymer electrolyte fuel cell 34 includes an anode 34A, a cathode 34B, and a polymer electrolyte 34C provided between these electrodes. The above-produced hydrogen gas, and air fed from an air blower 35 are supplied to the anode and the cathode, respectively, after the hydrogen gas and the air are, if necessary, subjected to appropriate humidification treatment (a humidifier is not illustrated).

In the anode, the hydrogen gas is converted into protons and electrons are released, whereas in the cathode, oxygen gas and the thus-released electrons and protons form water. Through these reactions, direct current flows between the electrodes 34A and 34B. The anode is formed of, for example, platinum black, a Pt-supported-on-activated carbon catalyst, or a Pt—Ru alloy catalyst. The cathode is formed of, for example, platinum black or a Pt-supported-on-activated carbon catalyst.

A burner 31A of the reformer 31 can be connected to the anode 34A for employing excess hydrogen as a fuel. A gas-water separator 36 connected to the cathode 34B is employed for separation of exhaust gas and water formed through bonding between hydrogen and oxygen contained in the air supplied to the cathode 34B. The thus-separated water may be employed for water vapor production.

An exhaust heat recovery apparatus 37 can be provided on the fuel cell 34 for recovery and effective utilization of heat generated in the fuel cell associated with electric power generation. The exhaust heat recovery apparatus 37 includes a heat exchanger 37A for recovering heat generated during the course of reaction; a heat exchanger 37B for transferring the heat recovered by the heat exchanger 37A to water; a condenser 37C; and a pump 37D for circulating a cooling medium through the heat exchangers 37A and 37B and the condenser 37C. Hot water obtained in the heat exchanger 37B may be effectively employed in, for example, equipment other than the fuel cell system.

EXAMPLES

The present invention will next be described with reference to Examples and Comparative Example.

As described below, color testing was performed by use of each of coloration agent for carbonyl sulfides obtained in the Examples and Comparative Example.

A coloration agent for carbonyl sulfide was formed into particles having a length of 0.5 to 1 mm, and the thus-formed coloration agent for carbonyl sulfide particles (1 mL) were charged into a reaction tube having an inner diameter of 9 mm. Subsequently, the temperature of the coloration agent for carbonyl sulfide was maintained at 25° C. at ambient pressure, and propane gas was caused to flow through the reaction tube at a GHSV of 12,000 $h^{-1}$ for 30 minutes. Subsequently, propane gas containing 50 vol. ppm carbonyl sulfide was caused to flow through the reaction tube at a GHSV of 12,000 $h^{-1}$ for one hour, followed by observation of color change, and measurement of the carbonyl sulfide content of the gas discharged from the outlet of the reaction tube by means of gas chromatography (sulfur chemiluminescence detector: SCD).

Example 1

A solution prepared by dissolving 470 g of cerium nitrate hexahydrate (special grade, product of Wako Pure Chemical Industries, Ltd) in one liter of heated water at a temperature of 50° C., water being purified with ion-exchange resin and 3 mol/L concentration of NaOH aqueous solution were dropwise added in a vessel and mixed so as to maintain pH 13 of the mixture. The resultant mixture was stirred for one hour while its temperature was maintained at 50° C. Subsequently, the resultant solid product was separated through filtration, and then washed with ion-exchange water (20 L), followed by drying of the solid product in an air blower/dryer at 110° C. for 12 hours, and calcination at 350° C. for three hours. Thereafter, the thus-calcined product was formed into a coloration agent for carbonyl sulfide through tableting, followed by pulverization, to thereby yield a light yellow coloration agent for carbonyl sulfide A having a mean particle size of 0.8 mm.

Example 2

Alumina (KHD-24, product of Sumitomo Chemical Co., Ltd.) (20 g) was impregnated with an aqueous solution prepared by dissolving silver nitrate (special grade, product of Wako Pure Chemical Industries, Ltd.) (3.5 g) in water (4 mL) so that silver was supported on alumina. Thereafter, the resultant product was dried in an air blower/dryer at 60° C. for three hours and at 120° C. for 12 hours, followed by calcination at 400° C. for three hours. The thus-calcined product was subjected to pulverization and granulation, to thereby yield a light brown coloration agent for carbonyl sulfide B having a mean particle size of 0.8 mm and containing 9.6 mass % of Ag.

Example 3

Alumina (KHD-24, product of Sumitomo Chemical Co., Ltd.) (20 g) was impregnated with an aqueous solution prepared by dissolving copper nitrate trihydrate (special grade, product of Wako Pure Chemical Industries, Ltd.) (8.5 g) in water (6 mL) so that copper was supported on alumina. Thereafter, the resultant product was dried in an air blower/dryer at 60° C. for three hours and at 120° C. for 12 hours, followed by calcination at 400° C. for three hours. The thus-calcined product was subjected to pulverization and granulation, to thereby yield a blue-green coloration agent for carbonyl sulfide C having a mean particle size of 0.8 mm and containing 9.3 mass % of Cu.

Example 4

Alumina (KHD-24, product of Sumitomo Chemical Co., Ltd.) (20 g) was impregnated with an aqueous solution prepared by dissolving nickel nitrate hexahydrate (special grade, product of Wako Pure Chemical Industries, Ltd.) (11 g) in water (5 mL) so that nickel was supported on alumina. Thereafter, the resultant product was dried in an air blower/dryer at 60° C. for three hours and at 120° C. for 12 hours, followed by calcination at 400° C. for three hours. The thus-calcined product was subjected to pulverization and granulation, to thereby yield a light green coloration agent for carbonyl sulfide D having a mean particle size of 0.8 mm and containing 9.1 mass % of Ni.

Example 5

Alumina (KHD-24, product of Sumitomo Chemical Co., Ltd.) (20 g) was impregnated with an aqueous solution prepared by dissolving iron nitrate nonahydrate (special grade, product of Wako Pure Chemical Industries, Ltd.) (16 g) in water (5 mL) so that iron was supported on alumina. Thereafter, the resultant product was dried in an air blower/dryer at 60° C. for three hours and at 120° C. for 12 hours, followed by calcination at 400° C. for three hours. The thus-calcined product was subjected to pulverization and granulation, to thereby yield a light reddish brown coloration agent for carbonyl sulfide E having a mean particle size of 0.8 mm and containing 9.5 mass % of Fe.

Comparative Example 1

Silver nitrate (7.9 g) was dissolved in ion-exchange water (100 mL). NaY zeolite (HSZ-320NAA, product of Tosoh Corporation) (20 g) was added to the above-prepared silver nitrate solution. The temperature of the resultant slurry was maintained at 50° C., and ion-exchange treatment was carried out for four hours under stirring, followed by filtration, washing with water, and then drying at 120° C. Subsequently, the resultant product was calcined at 400° C., to thereby yield Ag-exchanged Y zeolite containing 13.6 mass % of Ag. Thereafter, the zeolite was formed into tablets, and the tablets were pulverized, to thereby yield a white coloration agent for carbonyl sulfide F.

Each of the coloration agent for carbonyl sulfides obtained in the Examples and Comparative Example was subjected to color testing for the detection of carbonyl sulfide contained in propane gas. The results are shown in Table 1.

TABLE 1

| Coloration agent for carbonyl sulfide | Before use | After 30-minute flow of propane | After one-hour flow of COS + propane | Sulfur content at outlet (mass ppm) |
|---|---|---|---|---|
| Ex. 1 | A | Light yellow | Light yellow | Brown | <0.1 |
| Ex. 2 | B | Light brown | Light brown | Brown | <0.1 |
| Ex. 3 | C | Blue-green | Blue-green | Brown | <0.1 |
| Ex. 4 | D | Light green | Light green | Brown | <0.1 |
| Ex. 5 | E | Light reddish brown | Light reddish brown | Brown | 5 |
| Comp. Ex. 1 | F | White | White | White | 50 |

Note:
COS represents carbonyl sulfide.

Carbonyl sulfide contained in a hydrocarbon compound was visually detected by use of the coloration agent for carbonyl sulfide of the present invention, and leakage of carbonyl sulfide toward the downstream side was suppressed during observation of color development.

INDUSTRIAL APPLICABILITY

The present invention can provide a coloration agent for carbonyl sulfide which has the ability to develop a color in the presence of carbonyl sulfide contained in, for example, a fuel for fuel cells, which exhibits excellent performance in detecting carbonyl sulfide contained in the fuel, and which enables the service life of a desulfurizing agent to be determined through visual observation; carbonyl sulfide detection means including the coloration agent for carbonyl sulfide; and a fuel cell system including the detection means.

The invention claimed is:

1. A coloration agent for carbonyl sulfide comprising a metal oxide and, supported on the metal oxide, at least one metal component selected from among a cerium component, a silver component, a copper component, a nickel component, and an iron component.

2. The coloration agent for carbonyl sulfide as described in claim 1, wherein the metal oxide is at least one metal oxide or metal composite oxide selected from among ceria, alumina, silica, silica-alumina, zirconia, titania, and magnesia.

3. A coloration agent for carbonyl sulfide comprising at least one oxide selected from among a cerium oxide, a silver oxide, a copper oxide, a nickel oxide, and an iron oxide.

* * * * *